(12) United States Patent
Wall et al.

(10) Patent No.: US 6,268,375 B1
(45) Date of Patent: Jul. 31, 2001

(54) 10,11-DIFLUOROMETHYLENEDIOXYCAMPTOTHECIN COMPOUNDS WITH TOPOISOMERASE I INHIBITION

(75) Inventors: Monroe E. Wall, Chapel Hill; Mansukh C. Wani, Durham; Govindarajan Manikumar, Raleigh, all of NC (US); Neelakantan Balasubramanian; Dolatrai Vyas, both of Madison, CT (US)

(73) Assignees: Research Triangle Institute, Research Triangle Park, NC (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/474,758

(22) Filed: Dec. 29, 1999

(51) Int. Cl.$^7$ ................. A61K 31/4741; C07D 491/147; C07D 491/22
(52) U.S. Cl. ........................... 514/279; 546/41; 435/184; 435/233
(58) Field of Search ............... 514/279; 546/41; 435/184, 233

(56) References Cited

U.S. PATENT DOCUMENTS

| | | | |
|---|---|---|---|
| 4,894,456 | 1/1990 | Wall et al. | 546/41 |
| 4,981,968 | 1/1991 | Wall et al. | 544/361 |
| 5,049,668 | 9/1991 | Wall et al. | 540/481 |
| 5,053,512 | 10/1991 | Wani et al. | 546/41 |
| 5,106,742 | 4/1992 | Wall et al. | 435/233 |
| 5,122,526 | 6/1992 | Wall et al. | 514/253 |
| 5,122,606 | 6/1992 | Wani et al. | 546/41 |
| 5,180,722 | 1/1993 | Wall et al. | 514/219 |
| 5,224,903 | 7/1993 | Langhof et al. | 474/152 |
| 5,227,380 | 7/1993 | Wall et al. | 514/253 |
| 5,340,817 | 8/1994 | Wall et al. | 514/279 |
| 5,364,858 | 11/1994 | Wall et al. | 514/279 |
| 5,401,747 | 3/1995 | Wall et al. | 514/283 |
| 5,496,830 | 3/1996 | Shapiro et al. | 514/283 |
| 5,614,529 | 3/1997 | Wall et al. | 514/279 |
| 5,646,159 | 7/1997 | Wall et al. | 514/279 |
| 5,932,588 | 8/1999 | Wall et al. | 514/279 |
| 5,985,888 | 11/1999 | Wall et al. | 514/283 |

OTHER PUBLICATIONS

Brangi, M. et al. : Camptothecin resistance : Role of the ATP–binding cassette, Mitoxantrone–resistance half–transporter, and potential for glucuronidation in MXR–expressing cells. Cancer Research, vol. 59, pp. 5938–5946, Dec. 1, 1999.*

* cited by examiner

*Primary Examiner*—Charandlt S. Aulakh
(74) *Attorney, Agent, or Firm*—Oblon, Spivak, McClelland, Maier & Neustadt, P.C.

(57) ABSTRACT

Camptothecin compounds having a $C_{10,11}$ O—$(CF_2)_n$O group where n is 1 or 2 are effective anti-tumor compounds. These compounds inhibit the enzyme topoisomerase I and may alkylate DNA of the associated topoisomerase I-DNA cleavable complex.

10 Claims, 1 Drawing Sheet

FIG. 1

10, 11-DIFLUOROMETHYLENEDIOXYCAMPTOTHECIN COMPOUNDS WITH TOPOISOMERASE I INHIBITION

BACKGROUND OF THE INVENTION

1. Field of the Invention

This invention relates to fluorinated camptothecin compounds which inhibit the enzyme topoisomerase I and have anticancer activity. This invention is also related to the treatment of tumors in animals with camptothecin compounds.

2. Background of the Invention

Camptothecin (CPT) is a naturally occurring cytotoxic alkaloid which is known to inhibit the enzyme topoisomerase I and is a potent anti-tumor agent. Camptothecin compounds have the general ring structure shown below.

Camptothecin was isolated from the wood and bark of *Camptotheca acuminata* by Wall et al. (Wall et al., 1966, J. Am. Chem. Soc., 88:3888).

Major synthetic efforts have been directed to derivatizing the A-ring and/or the B-ring to improve cytotoxic activity and to improve water-solubility.

The cytotoxic activity of camptothecin compounds is believed to arise from the ability of these compounds to inhibit both DNA and RNA synthesis and to cause reversible fragmentation of DNA in mammalian cells. Topoisomerase I relaxes both positively and negatively supercoiled DNA and has been implicated in various DNA transactions such as replication, transcription and recombination. The enzyme mechanism is believed to involve a transient breakage of one of the two DNA strands and the formation of a reversible covalent topoisomerase I enzyme-DNA complex. Camptothecin interferes with the DNA breakage-reunion reaction by reversibly trapping the enzyme-DNA intermediate termed the "cleavable complex". The cleavable complex assay is a standard test for determining the cytotoxic activity of camptothecin compounds. The high levels of topoisomerase I in several types of human cancer and the low levels in correspondingly normal tissue provide the basis for tumor treatment with biologically active camptothecin analogs.

U.S. Pat. No. 4,894,456 describes methods of synthesizing camptothecin compounds which act as inhibitors of topoisomerase I and are effective in the treatment of leukemia (L-1210). U.S. Pat. No. 5,225,404 discloses methods of treating colon tumors with camptothecin compounds.

Numerous camptothecin compounds and their use as inhibitors of topoisomerase I are reported by U.S. Pat. No. 5,053,512; U.S. Pat. No. 4,981,968; U.S. Pat. No. 5,049,668; U.S. Pat. No. 5,106,742; U.S. Pat. No. 5,180,722; U.S. Pat. No. 5,244,903; U.S. Pat. No. 5,227,380; U.S. Pat. No. 5,122,606; U.S. Pat. No. 5,122,526; and U.S. Pat. No. 5,340,817.

U.S. Pat. No. 4,943,579 discloses the esterification of the hydroxyl group at the 20-position of camptothecin to form several prodrugs. This patent further discloses that the prodrugs are water soluble and are converted into the parent camptothecin compounds by hydrolysis.

Brangi et al., *Cancer Research*, 59, 5938–5946 Dec. 1, 1999, reports an investigation of Camptothecin resistance in cancer cells and reports the compound difluoro-10, 11-methylenedioxy-20(S)-camptothecin.

A need continues to exist, however, for camptothecin compounds having improved activity.

SUMMARY OF THE INVENTION

Accordingly, one object of the present invention is to provide camptothecin compounds having improved and novel biological activity and reduced toxicity.

Another object of the present invention is to provide a method of treating leukemia or solid tumors in a mammal in need thereof by administration of a camptothecin compound.

Another object of the present invention is to provide a method of inhibiting the enzyme topoisomerase I and/or alkylating DNA of associated DNA-topoisomerase I by contacting a DNA-topoisomerase I complex with a camptothecin compound.

These and other objects of the present invention are made possible by camptothecin compounds having the structure:

where

X and Y are each independently $NO_2$, $NH_2$, H, F, Cl, Br, I, COOH, OH, O—$C_{1-6}$alkyl, SH, S—$C_{1-6}$alkyl, CN, NH—$C_{1-6}$alkyl, N($C_{1-6}$alkyl)$_2$, CHO, $C_{1-8}$alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$alkyl$)_2$ wherein Z is selected from the group consisting of O, NH and S, and a is an integer of 2 or 3, —$CH_2$—L, where L is halogen (F, Cl, Br, I), $^+N_2$, $^+(OR^1)_2$, $^+N(R^1)_3$, $OC(O)R^1$, $OSO_2R^1$, $OSO_2CF_3$, $OSO_2C_4F_9$, $C_{1-6}$alkyl-C—(=O)—, $C_{4-18}$aryl-C(=O)—, $C_{1-6}$alkyl-$SO_2$—, perfluoro $C_{1-6}$alkyl-$SO_2$— and $C_{4-18}$aryl-$SO_2$—, (where each $R^1$ independently is $C_{1-6}$alkyl, $C_{4-18}$aryl or $C_{4-18}$Ar$C_{1-6}$alkyl); or —$CH_2NR^2R^3$, where (a) $R^2$ and $R^3$ are, independently, hydrogen, $C_{1-6}$alkyl, $C_{3-7}$ cycloalkyl, $C_{3-7}$cycloalkyl-$C_{1-6}$alkyl, $C_{2-6}$alkenyl, hydroxy-$C_{1-6}$alkyl, $C_{1-6}$alkoxy-$C_{1-6}COR^4$ where $R^4$ is hydrogen, $C_{1-6}$alkyl, perhalo-$C_{1-6}$alkyl, $C_{3-7}$cycloalkyl, $C_{3-7}$cycloalkyl-$C_{1-6}$alkyl, $C_{2-6}$alkenyl, hydroxy-$C_{1-6}$alkyl, $C_{1-6}$alkoxy, $C_{1-6}$alkoxy-$C_{1-6}$alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$alkyl, perhalo-$C_{1-6}$alkyl, aryl, aryl substituted with one or more groups selected from the group consisting of $C_{1-6}$alkyl, halogen, nitro, amino, $C_{1-6}$alkylamino, perhalo-$C_{1-6}$alkyl, hydroxy-$C_{1-6}$alkyl, $C_{1-6}$alkoxy, $C_{1-6}$alkoxy-$C_{1-6}$alkyl and —COR$^6$ where R$^6$ is hydrogen, $C_{1-6}$alkyl perhalo-$C_{1-6}$alkyl, $C_{1-6}$alkoxy, aryl, and aryl substituted with one or more $C_{1-6}$alkyl, perhalo-$C_{1-6}$ alkyl, hydroxy-$C_{1-6}$alkyl, or $C_{1-6}$alkoxy-$C_{1-6}$alkyl groups;

R$^7$ is H, or C(O)—(CH$_2$)$_m$—NR$^8$R$^9$, where m is an integer of 1–6 or —C(O)CHR$^{10}$NR$^8$R$^9$, where R$^{10}$ is the side chain of one of the naturally occurring α-amino acids, R$^8$ and R$^9$ are, independently, hydrogen, $C_{1-8}$alkyl or —C(O)CHR$^{11}$NR$^{12}$R$^{13}$, where R$^{11}$ is the side chain of one of the naturally occurring α-amino acids and R$^{12}$ and R$^{13}$ are each independently hydrogen or $C_{1-8}$alkyl; and n is an integer of 1 or 2, and salts thereof.

10,11-Difluoromethylenedioxycamptothecin is a potent inhibitor of topoisomerase I, being of the same order as 10,11-methylenedioxycamptothecin (i.e about 10 times camptothecin). Moreover, there has been concern that the 10,11-methylene dioxy ring may be metabolically cleaved to the corresponding catechol by cytochrome P450. However, it is well known that substitution of hydrogen by fluorine renders P450 metabolism relatively negligible. In a number of cases, 10,11-difluoromethylenedioxy compounds administered either iv or orally have shown less GI toxicity than other camptothecin analogs and have shown excellent activity against a number of mouse cancer cell lines, both in vitro and in vivo.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Unless indicated to the contrary, the term "alkyl" as used herein means a straight-chain or branched chain alkyl group with 1–30, preferably 1–18 carbon atoms, m ore preferably 1–8 carbon atoms, including methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. The term "alkyl" also includes $C_{3-30}$cycloalkyl groups such as cyclopropyl, cyclopentyl, cyclohexyl, cycloheptyl and cyclooctyl groups.

Unless indicated to the contrary, the term "aryl" as used herein means a carbocyclic aromatic ring having 6–18 carbon atoms, preferably 6–10 carbon atoms in the aromatic ring structure. The aromatic rings may be substituted by one or more alkyl group, preferably alkyl groups having 1–10 carbon atoms. A particularly preferred aryl group is phenyl.

Unless indicated to the contrary, the term "aralkyl" as used herein means a straight-chain or branched chain alkyl group as defined above for the term "alkyl" bonded to an aryl group as defined above for the term "aryl". Preferred aralkyl groups are benzyl, phenethyl, etc.

As used herein, the term "acyl" means formyloxy and acyl moieties derived from aromatic carboxylic acids, heterocyclic carboxylic acids, aralkyl carboxylic acids, as well as alkyl and aromatic sulfonic acids. The alkyl groups of these acyloxy moieties may be a straight-chain or branched-chain alkyl group with 1–7 carbon atoms. Additionally, the acyl moiety may contain one or more unsaturated carbon-carbon bonds and may also carry one or more substituents such as halogen, amino and hydroxyl groups.

The camptothecin compounds of the present invention may bear a leaving group at one or more of the positions $C_7$ or $C_9$ of the camptothecin ring structure. More specifically, the leaving group is a group of the formula —CH$_2$—L, where L is a functional group which can be easily displaced, i.e. L is a good leaving group in nucleophilic substitution reactions. Suitable groups L include halogen (F, Cl, Br, I), $^+$N$_2$, $^+$(OR$^1$)$_2$, $^+$S(R$^1$)$_2$, $^+$N(R$^1$)$_3$, OC(O)R$^1$, OSO$_2$R$^1$, OSO$_2$CF$_3$, and OSO$_2$C$_4$F$_9$, $C_{1-6}$alkyl-C(=O)—, $C_{4-18}$aryl-C(=O)—, $C_{1-6}$alkyl-SO$_2$—, perfluoro $C_{1-6}$alkyl-SO$_2$— and $C_{4-18}$aryl-SO$_2$—, (where each R$^1$ independently is $C_{1-6}$alkyl, $C_{4-18}$ aryl or $C_{4-18}$ArC$_{1-6}$alkyl).

While not being bound by any particular theory, it is believed that nucleophilic groups on DNA displace leaving group L from the camptothecin compounds of the present invention resulting in alkylation of the DNA by the alkylating group of the camptothecin ring structure. Suitable nucleophilic groups present in DNA include the nucleophilic groups found in DNA bases adenine, guanine, thymine, and cytosine, such as NH$_2$, —NH— and =N— groups. When a camptothecin compound of the invention having a —CH$_2$—L group is contacted with DNA, nucleophilic displacement of leaving group L results in alkylation of the nucleic acid. The compounds of the present invention exhibit a novel anti-tumor activity by alkylating DNA.

Camptothecin compounds have an asymmetric carbon atom at the 20-position making two enantiomeric forms, i.e., the (R) and the (S) configurations, possible. This invention includes both enantiomeric forms and any combinations or mixtures of these forms. The invention also includes other forms of the camptothecin compounds including solvates, hydrates, polymorphs, salts, etc. Particularly preferred compounds are camptothecin derivatives having the (S) configuration at the 20-position.

In a preferred embodiment, X is NO$_2$, NH$_2$, H, F, Cl, Br, I, COOH, OH, O—$C_{1-6}$alkyl, SH, S—$C_{1-6}$alkyl, CN, CH$_2$NH$_2$, NH—$C_{1-6}$alkyl, CH$_2$NHC$_{1-6}$alkyl, N(C$_{1-6}$alkyl)$_2$, CH$_2$N(C$_{1-6}$ alkyl)$_2$, O—CH$_2$CH$_2$N(CH$_2$CH$_2$OH)$_2$, NH—CH$_2$CH$_2$N(CH$_2$CH$_2$OH)$_2$, S—CH$_2$CH$_2$N (CH$_2$CH$_2$OH)$_2$, O—CH$_2$CH$_2$CH$_2$N(CH$_2$CH$_2$OH)$_2$, NH—CH$_2$CH$_2$CH$_2$N(CH$_2$CH$_2$OH)$_2$, S—CH$_2$CH$_2$CH$_2$N (CH$_2$CH$_2$OH)$_2$, O—CH$_2$CH$_2$N(CH$_2$CH$_2$CH$_2$OH)$_2$, NH—CH$_2$CH$_2$N(CH$_2$CH$_2$CH$_2$OH)$_2$, S—CH$_2$CH$_2$N (CH$_2$CH$_2$CH$_2$OH)$_2$, O—CH$_2$CH$_2$CH$_2$N(CH$_2$CH$_2$CH$_2$OH$_2$)$_2$, NH—CH$_2$CH$_2$CH$_2$N(CH$_2$CH$_2$CH$_2$OH$_2$)$_2$, S—CH$_2$CH$_2$CH$_2$N(CH$_2$CH$_2$CH$_2$OH$_2$)$_2$, O—CH$_2$CH$_2$N (C$_{1-6}$alkyl)$_2$, NH—CH$_2$CH$_2$N(C$_{1-6}$alkyl)$_2$, S—CH$_2$CH$_2$N (C$_{1-6}$alkyl)$_2$, O—CH$_2$CH$_2$CH$_2$N(C$_{1-6}$alkyl)$_2$, NH—CH$_2$CH$_2$CH$_2$N(C$_{1-6}$alkyl)$_2$, S—CH$_2$CH$_2$CH$_2$N (C$_{1-6}$alkyl)$_2$, CHO, N$_2$, $C_{1-8}$alkyl, CH$_2$—L where L is halogen (F, Cl, Br, I), $^+$N$_2$, $^+$(OR$^1$)$_2$ (where each R$^1$ independently is alkyl, aryl or aralkyl as defined above), $^-$S(R$^1$)$_2$, $^+$N(R$^1$)$_3$, OC(O)R$^1$, OSO$_2$R$^1$, OSO$_2$CF$_3$, OSO$_2$C$_4$F$_9$, $C_{1-6}$alkyl-C(=O)—, $C_{4-18}$aryl-C(=O)—, $C_{1-6}$alkyl-SO$_2$—, perfluoro $C_{1-6}$alkyl-SO$_2$— and $C_{4-18}$aryl-SO$_2$—.

In a preferred embodiment Y is H, $C_{1-8}$alkyl, or CH$_2$NR$^2$R$^3$ where (a) R$^2$ and R$^3$ are, independently, hydrogen, $C_{1-6}$alkyl, $C_{3-7}$cycloalkyl, $C_{3-7}$cycloalkyl-$C_{1-6}$alkyl, $C_{2-6}$alkenyl, hydroxy-$C_{1-6}$alkyl, $C_{1-6}$alkoxy-$C_{1-6}$COR$^4$ where R$^4$ is hydrogen, $C_{1-6}$alkyl, perhalo-$C_{1-6}$alkyl, $C_{3-7}$cycloalkyl, $C_{3-7}$cycloalkyl-$C_{1-6}$alkyl, $C_{2-6}$alkenyl, hydroxy-$C_{1-6}$alkyl, $C_{1-6}$alkoxy, $C_{1-6}$alkoxy- $C_{1-6}$alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$alkyl, perhalo-$C_{1-6}$alkyl, aryl, aryl substituted with one or more groups selected from the group consisting of $C_{1-6}$alkyl, halogen, nitro, amino, $C_{1-6}$ alkylamino, perhalo-$C_{1-6}$alkyl, hydroxy-$C_{1-6}$alkyl, $C_{1-6}$alkoxy, $C_{1-6}$alkoxy-$C_{1-6}$alkyl and —$COR^6$ where $R^6$ is hydrogen, $C_{1-6}$alkyl perhalo-$C_{1-6}$alkyl, $C_{1-6}$alkoxy, aryl, and aryl substituted with one or more $C_{1-6}$alkyl, perhalo-$C_{1-6}$alkyl, hydroxy-$C_{1-6}$alkyl, or $C_{1-6}$alkoxy-$C_{1-6}$alkyl groups.

The group $R^7$ may be an ester of a naturally occurring or non-naturally occurring amino acid such as an ester of glycine or β-alanine. In particular, the present invention is directed to camptothecin compounds where the group $R^7$ is $C(O)$—$(CH_2)_m$—$NR^8R^9$, where m is the integer 1, 2, 3, 4, 5 and 6 and $R^8$ and $R^9$ are each H.

Suitable side chains $R^{10}$ and $R^{11}$ appearing on the group $R^7$ are the side chains of the amino acids glycine, α-alanine, β-alanine, valine, leucine, isoleucine, phenylalanine, tyrosine, tryptophan, lysine, arginine, histidine, asparate, glutamate, asparagine, glutamine, cysteine and methionine. Moreover, the group $R^7$, may comprise two amino acid units linked by a peptide linkage. In particular the group $R^7$ may comprise a β-alanine group linked to a lysine of the structure Moreover, the group $R^7$ may provide basis for the formation of a mono or di salts, via the free amine groups, such as a hydrochloride or dihydrochloride.

A synthon for attaching such a group to a terminal hydroxyl group is described by Hudkins et al. *Bioorg. Med. Chem. Lett,* 8(1988)1873–1876).

Particularly preferred esters are glycinate esters and the peptide ester based on β-alanine-lysine. These esters are pro-drugs which are converted to the camptothecin compound by hydrolysis of the ester bond. The esters may be prepared by the method described in U.S. Pat. No. 4,943,579 which is incorporated herein by reference for a more complete description of the process of preparing the esters and for a description of suitable esters formed by the process. The esterification synthon may need to introduced in a protected form, such that the reaction of amine groups is inhibited, followed by removal of the protecting group. Such protecting groups are well known to those of ordinary skill in the art and are described by Hudkins et al. *Bioorg. Med. Chem. Lett,* 8(1998)1873–1876).

Specific examples of non-limiting compounds include 10,11-difluoromethylenedioxy-20-(S)-camptothecin; 7-ethyl 10,11-difluoromethylenedioxy-20(S)-camptothecin; 7-chloromethyl 10,11-difluoromethylenedioxy-20-(S)-camptothecin; 7-bromomethyl 10,11-difluoromethylenedioxy-20-(S)-camptothecin; 7-hydroxymethyl-10,11-difluoromethylenedioxy-20-(S)-camptothecin, 9-nitro 10,11-difluoromethylenedioxy-20-(S)-camptothecin, 9-amino 10,11-difluoromethylenedioxy-20-(S)-camptothecin, 7-ethyl-9-nitro 10,11-difluoromethylenedioxy-20-(S)-camptothecin and 7-ethyl-9-amino 10,11-difluoromethylenedioxy-20-(S)-camptothecin.

Specific non-limiting examples further include the $C_{20}$ amino acid ester of the above identified compounds 10,11-difluoromethylenedioxy-20-O-glycinyl-20-(S)-camptothecin; 7-ethyl 10,11-difluoromethylenedioxy-20-O-glycinyl-20-(S)-camptothecin; 7-chloromethyl 10,11-difluoromethylenedioxy-20-O-glycinyl-20-(S)-camptothecin; 7-bromomethyl 10,11-difluoromethylenedioxy-20-O-glycinyl-20-(S)-camptothecin; 7-hydroxymethyl-10,11-difluoromethylenedioxy-20-O-glycinyl-20-(S)-camptothecin, 9-nitro 10,11-difluoromethylenedioxy-20-O-(S)-camptothecin, 9-amino 10,11-difluoromethylenedioxy-20-O-glycinyl-20-(S)-camptothecin, 7-ethyl-9-nitro 10,11-difluoromethylenedioxy-20-O-glycinyl-20-(S)-camptothecin, 7-ethyl-9-amino 10,11-difluoromethylenedioxy-20-glycinyl-20-(S)-camptothecin,

10,11-difluoromethylenedioxy-20-O-N-methylglycinyl-20-(S)-camptothecin; 7-ethyl 10,11-difluoromethylenedioxy-20-O-N-methylglycinyl-20-(S)-camptothecin; 7-chloromethyl 10,11-difluoromethylenedioxy-20-O-N-methylglycinyl-20-S)-camptothecin; 7-bromomethyl 10,11-difluoromethylenedioxy-20-O-N-methylglycinyl-20-(S)-camptothecin; 7-hydroxymethyl-10,11-difluoromethylenedioxy-20-O-N-methylglycinyl-20-(S)-camptothecin, 9-nitro 10,11-difluoromethylenedioxy-20-O-N-methylglycinyl-20-(S)-camptothecin, 9-amino 10,11-difluoromethylenedioxy-20-O-N-methylglycinyl-20-(S)-camptothecin, 7-ethyl-9-nitro 10,11-difluoromethylenedioxy-20-O-N-methylglycinyl-20-(S)-camptothecin, 7-ethyl-9-amino 10,11-difluoromethylenedioxy-20-O-N-methylglycinyl-20-(S)-camptothecin, 10,11-difluoromethylenedioxy-20-O-N,N-dimethylglycinyl-20-(S)-camptothecin; 7-ethyl 10,11-difluoromethylenedioxy-20-O-N,N-dimethylglycinyl-20-(S)-camptothecin; 7-chloromethyl 10,11-difluoromethylenedioxy-20-O-N,N-dimethylglycinyl-20-(S)-camptothecin; 7-bromomethyl 10,11-difluoromethylenedioxy-20-O-N,N-dimethylglycinyl-20-(S)-camptothecin; 7-hydroxymethyl-10,11-difluoromethylenedioxy-20-O-N,N-dimethylglycinyl-20-(S)-camptothecin, 9-nitro 10,11-difluoromethylenedioxy-20-O-N,N-dimethylglycinyl-20-(S)-camptothecin, 9-amino 10,11-difluoromethylenedioxy-20-O-N,N-dimethylglycinyl-20-(S)-camptothecin, 7-ethyl-9-nitro 10,11-difluoromethylenedioxy-20-O-N,N-dimethylglycinyl-20-(S)-camptothecin and 7-ethyl-9-amino 10,11-difluoromethylenedioxy-20-O-N,N-dimethylglycinyl-20-(S)-camptothecin.

Additional specific non-limiting examples further include 10,11-difluoromethylenedioxy-20-O-β-ala-lys-20-(S)-camptothecin; 7-ethyl 10,11-difluoromethylenedioxy-20-O-β-ala-lys-20-(S)-camptothecin; 7-chloromethyl 10,11-difluoromethylenedioxy-20-O-β-ala-lys-20-(S)-camptothecin; 7-bromomethyl 10,11-difluoromethylenedioxy-20-O-β-ala-lys-20-(S)-camptothecin; 7-hydroxymethyl-10,11-difluoromethylenedioxy-20-O-β-ala-lys-20-(S)-camptothecin, 9-nitro 10,11-difluoromethylenedioxy-20-O-β-ala-lys-20-(S)-camptothecin, 9-amino 10,11-difluoromethylenedioxy-20-O-β-ala-lys-20-(S)-camptothecin, 7-ethyl-9-nitro 10,11-difluoromethylenedioxy-20-O-β-ala-lys-20-(S)-camptothecin and 7-ethyl-9-amino 10,11-difluoromethylenedioxy-20-O-β-ala-lys-20-(S)-camptothecin.

Additional specific non-limiting examples further include 10,11-difluoromethylenedioxy-20-O-β-ala-20-(S)-camptothecin; 7-ethyl 10,11-difluoromethylenedioxy-20-O-β-ala-20-(S)-camptothecin; 7-chloromethyl 10,11-difluoromethylenedioxy-20-O-β-ala-20(S)-camptothecin; 7-bromomethyl 10,11-difluoromethylenedioxy-20-O-β-ala-20-(S)-camptothecin; 7-hydroxymethyl-10,11-difluoromethylenedioxy-20-O-β-ala-20-(S)-camptothecin, 9-nitro 10,11-difluoromethylenedioxy-20-O-β-ala-20-(S)-camptothecin, 9-amino 10,11-difluoromethylenedioxy-20-O-β-ala-20-(S)-camptothecin, 7-ethyl-9-nitro 10,11-difluoromethylenedioxy-20-O-β-ala-20-S)-camptothecin and 7-ethyl-9-amino 10,11-difluoromethylenedioxy-20-O-β-ala-20-(S)-camptothecin.

Within the scope of the present invention, the lactone ring of the camptothecin compounds shown above may be opened by alkali metal or alkaline earth metal bases (MOH) for example, sodium hydroxide or calcium hydroxide to form alkali metal or alkaline earth metal salts of the open ring salt form of the camptothecin compounds.

Open ring compounds generally have better solubility in water. The group M may also be any pharmaceutically acceptable cation, obtained either directly by ring opening or by cation exchange of a ring open salt. Suitable groups M include $Li^+$, $Na^+$, $K^+$ and $Mg^{+2}$.

The compounds of the present invention may be prepared by conventional methods known to those of ordinary skill in the art, without undue experimentation.

The claimed compounds may be prepared by condensation of a perfluoroalkylenedioxybenzaldehyde of formula II (II)

Synthesis of the tetrafluoroethylenedioxy substituted compound would be by analogy to the illustrated difluoromethylenedioxy substituted compound supra by starting with 3,4-tetrafluoroethylenedioxy benzaldehyde.

Figure 1:
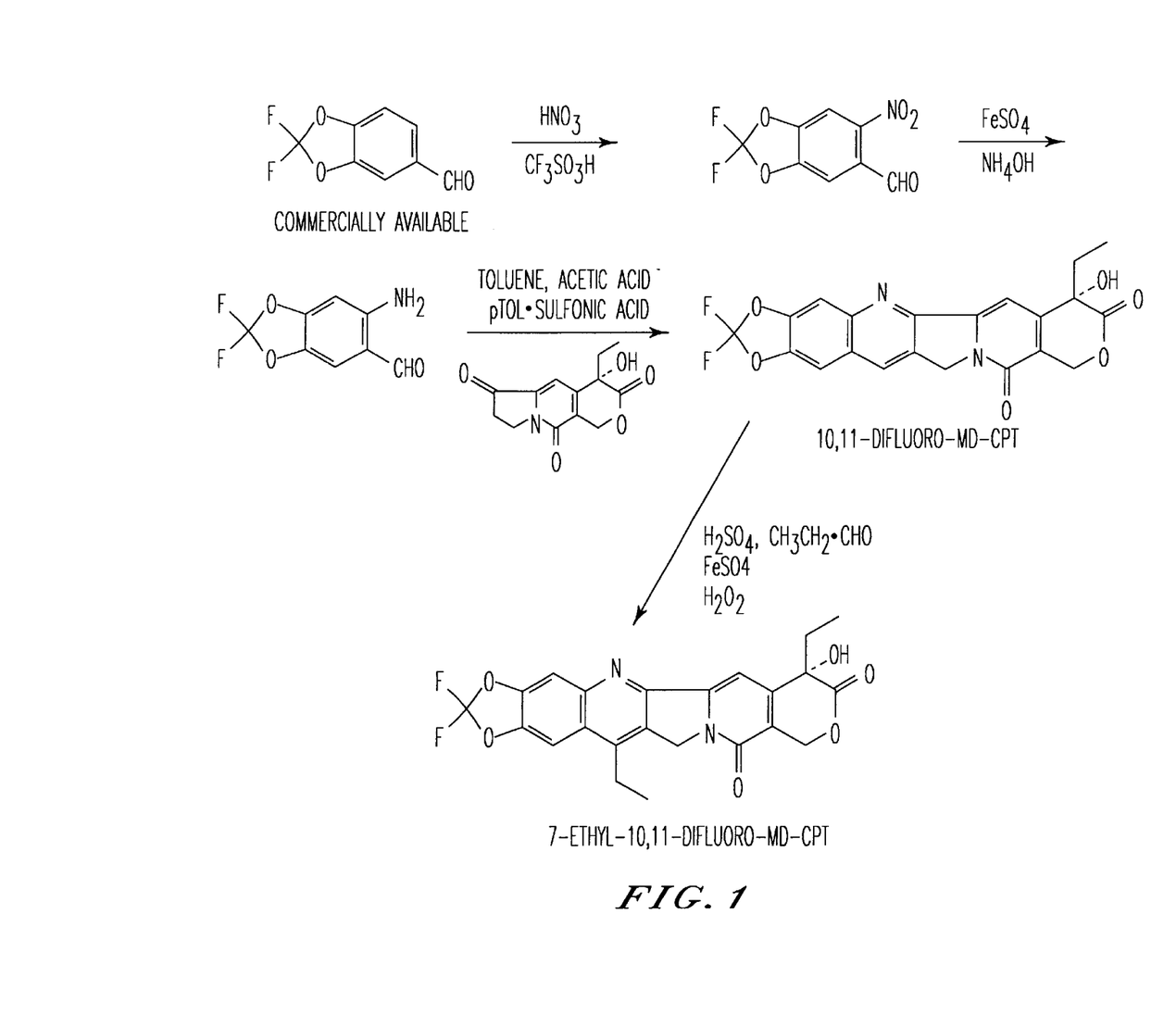
FIG. 1 illustrates a synthetic reaction scheme for preparing compounds according to the present invention.

For illustration purposes, a synthetic route is illustrated in FIG. 1, in which the A ring is substituted with a difluoromethylenedioxy group as a species of perfluoroalkylenedioxy group.

The corresponding perfluoroalkylenedioxy benzaldehyde may be converted to a perfluoroalkylenedioxy benzaldehyde bearing an α-amino group, via an α-nitro intermediate, by conventional methods known to those of ordinary skill in the art. Condensation with a tricyclic ketone of formula III yields the perfluoroalkylenedioxy substituted camptothecin.

(III)

Tricyclic ketone of formula III may be prepared by conventional methods known to those of ordinary skill in the art, such as that described by Wall et al. U.S. Pat. No. 5,122,526, the relevant portions of which are hereby incorporated by reference.

Substitution at the $C_7$ position may be conducted by condensation with the corresponding aldehyde of the $C_7$ substituent. Esterification with an amino acid at $C_{20}$ is possible by conventional methods known to those of ordinary skill in the art. Substitution at $C_9$ with groups such a nitro and amino is also possible in a manner analogous to that described in the literature.

The compounds of the invention have the group —$CH_2$—L at $C_9$ are prepared from known 20(S)-CPT compounds bearing a halogen, for example, a bromine atom, at the $C_9$ position. The halogen atom can be readily converted into the corresponding cyano analog by reaction with CuCN, followed by hydrolysis to form the corresponding carboxy analog. The carboxy analog is reduced to the corresponding hydroxy methyl analog which can be reacted with $Ph_3P$-$CCl_4$ to provide the corresponding chloromethyl analog. The chloromethyl analog can be readily converted to the bromomethyl and iodomethyl analogs using LiBr or LiI. The remaining compounds of the invention are prepared from these compounds by reaction with the corresponding acid chloride, sulfonyl chloride, etc. These reactions are well known to one having ordinary skill in this art.

Compounds in which L is Br or I are readily prepared from the compound in which L is Cl by simple halide exchange employing LiBr or LiI in dimethylformamide (DMF) solution (Larock, R. C., Comprehensive Organic Transformations, VCH Publishers, Inc., p. 337, N.Y. (1989).

Alternatively, the 7-methyl compounds (L is H) can be prepared either by a Friedlander reaction employing the corresponding acetophenone, or by a free radical alkylation reaction (Sawada et al., 1991, Chem. Phar. Bull., 39:2574). Free radical bromination of 7-methyl substrates can be accomplished by employing N-bromosuccinimide (NBS) in acetic acid (HOAc) under catalysis by benzoyl peroxide to give compounds in which L is Br.

9-Nitro-difluoro-10,11-methylenedioxy-20-(S)-camptothecin may be prepared from difluoro-10,11-methylenedioxy-20-(S)-camptothecin by treatment with $HNO_3$. 9-Amino difluoro-10,11-methylenedioxy-20-(S)-camptothecin may be prepared from 9-nitro difluoro-10,11-methylenedioxy-20-(S)-camptothecin via reduction with $SnCl_2$.

Other compounds which possess oxygen-derived leaving groups, such as triflate or tosylate, are prepared from the 7-hydroxymethyl and/or 7-halomethyl compounds. The 7-hydroxymethyl compounds are prepared from the corresponding parent compounds by the hydroxymethylation reaction. (e.g. Sawada et al., 1991, Chem. Pharm. Bull., 39:2574) Treatment of these compounds with readily available sulfonic acid chlorides or anhydrides using known procedures (Stang et al., 1982, Synthesis, 85) provides the highly electrophilic substrates noted above. Alternatively, the compounds described above can be generated from any of the substrates where L is Cl, Br or I by reaction with the silver salt of the corresponding acid (e.g., silver trifluoromethanesulfonate, silver tosylate, etc.) as described generally by Stang et al. and more specifically by Gramstad and Haszeldine (T. Gramstad and R. N. Haszeldine, 1956, J. Chem. Soc., 173).

$C_{20}$ esters may be prepared by esterifying the 20-position hydroxyl group of a camptothecin compound to form an ester containing a water-soluble moiety. Generally, the camptothecin compound is initially suspended in methylene chloride or other inert solvent, stirred and cooled. To the cooled mixture is added one equivalent of an acid having the formula $HOOC—CHR^{10}—NR^8R^9$ or $HOOC—(CH_2)_m—NR^8R^9$, where m is an integer from 1–6, preferably 2–6, and $R^{10}$ is the side chain of one of the naturally occurring α-amino acids. $R^8$ and $R^9$ are, independently, hydrogen or $C_{1-8}$alkyl. Suitable side chains $R^{10}$ are the side chains of the amino acids glycine, α-alanine, β-alanine, valine, leucine, isoleucine, phenylalanine, tyrosine, tryptophan, leucine, arginine, histidine, asparatate, glutamate, asparagine, glutamine, cysteine and methionine. Particularly preferred esters are glycinate esters. One equivalent of dicyclohexylcarbodiimide (DCC) and a catalytic amount of an amine base, preferably a secondary or tertiary amine, are also added to the mixture, which is then stirred to complete the reaction. Any precipitate which forms is removed by filtration and the product is isolated after removal of the solvent.

The free amine(s) may be converted to an acid addition salt by the addition of a pharmaceutically acceptable acid. Suitable acids include both inorganic and organic acids. Suitable addition salts include, but are not limited to hydrochloride, sulfate, phosphate, diphosphate, hydrobromide, nitrate, acetate, malate, maleate, fumarate tartrate, succinate, citrate, lactate, methanesulfonate, p-toluenesulfonate, palmoate, salicylate and stearate salts. The salts may be purified by crystallization from a suitable solvent.

The water-soluble 20-hydroxyl esters of the present invention are substantially less toxic than the parent compounds from which the esters are prepared.

The camptothecin compounds are administered in a dose which is effective to inhibit the growth of tumors. As used herein, an effective amount of the camptothecin compounds is intended to mean an amount of the compound that will inhibit the growth of tumors, that is, reduce the site of growing tumors relative to a control in which the tumor is not treated with the camptothecin compound. These effective amounts are generally from about 1–60 mg/kg of body weight per week, preferably about 2–20 mg/kg per week.

The compounds of the present invention may be administered as a pharmaceutical composition containing the camptothecin compound and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates an agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. For the purpose of oral therapeutic administration, the aforesaid compounds may be incorporated with excipients and used in the form of tablets, gelatine capsules, troches, capsules, elixirs, suspensions, syrups, wafers, chewing gums and the like. Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed. Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of the ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame, saccharin, or sucralose.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean licithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drugs with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

The compounds of the present invention may also be administered in the form of liposome or microvesicle preparations. Liposomes are microvesicles with encapsulate a liquid within lipid or polymeric membranes. Liposomes and methods of preparing liposomes are known and are described, for example, in U.S. Pat. No. 4,452,747, U.S. Pat. No. 4,448,765, U.S. Pat. No. 4,837,028, U.S. Pat. No. 4,721,612, U.S. Pat. No. 4,594,241, U.S. Pat. No. 4,302,459 and U.S. Pat. No. 4,186,183. The disclosures of these U.S. patents are incorporated herein by reference. Suitable liposome preparations for use in the present invention are also described in WO-9318749-A1, J-02056431-A and EP-276783-A.

The camptothecin compounds may be used individually to inhibit the growth of tumors. Alternatively, combinations of two or more camptothecin compounds may be used or combinations of one or more camptothecin compounds with one or more known anti-tumor compounds. When a camptothecin compound is combined with a conventional anti-tumor compound, the camptothecin compound will generally be present in an amount ranging from about 1–99wt. %, preferably, 5–95 wt. % of the combined amount of camptothecin and conventional anti-tumor compound. The pharmaceutical compositions noted above may contain these combinations of compounds together with an acceptable carrier or diluent.

The ester compounds of the invention may be administered to treat leukemia and solid tumors in mammals, including humans. The esters of the present invention are prodrugs which are hydrolyzed to camptothecin compounds demonstrating inhibitory activity on topoisomerase I. The camptothecin compounds formed by hydrolysis of the esters of the invention are also effective in treating leukemia and solid tumors in mammals. Numerous camptothecin compounds have been shown to be effective against leukemia using the standard L1210 leukemia assay (Wall et al. (1993), Journal of Medicinal Chemistry, 36:2689–2700). High activity of camptothecin and camptothecin analogs has also been shown in the P388 leukemia assay (Wall (1983), Medical and Pediatric Oncology, 11:480A–489A). The later reference also provides a correlation between anti-leukemia activity as determined by the L1210 and the P388 leukemia assays with efficacy of camptothecin compounds against solid tumors. Compounds reported as active in the leukemia assays also have demonstrated activity in a number of solid tumors including a color xenograft, a lung xenograft, a Walker sarcoma and a breast xenograft (Wall(1983), Table IV, page 484 A). Recent studies have confirmed the correlation between topoisomerase I inhibitory active and anti-leukemia/anti-tumor activity of camptothecin compounds (Giovanella et al. (1989), Science, 246: 1046–1048). The compounds of the present invention are particularly effective in the treatment of colon, lung, breast and ovary solid tumors, brain glioma and leukemia. These compounds may also be used to treat maleria.

Other features of the invention will become apparent in the coarse of the following descriptions of exemplary embodiments which are given for illustration of the invention and are not intended to be limiting thereof.

Throughout this experimental portion, the term DFMD will refer to difluoromethylendioxy.

1. 3,4-(Difluoromethylenedioxy)-6-nitrobenzaldehyde (3,4-DFMD-6-Nitrobenzaldehyde)

To a solution of trifluoromethanesulfonic acid (24 mL) in $CH_2Cl_2$ (300 mL) was added nitric acid (7.5 mL). A white solid separated from the solution. The suspension was cooled to −65° C. and 3,4-DFMD-benzaldehyde (5.1 g, 27.3 mmol) was added, dropwise. The mixture was stirred at −55 to −65° C. for 2 h, at 0° C. for 2 h, then left in the refrigerator overnight. The cool mixture was poured over ice and extracted with $CH_2Cl_2$. The combined organic layer was washed with water and dried to give the crude product which was purified by column chromatography on a silica gel column, using hexane-$CH_2Cl_2$-EtOAc(10:1:1) as the eluent. Fractions containing pure product were combined and concentrated to give 4.40 g (70%) of the title compound after crystallization from hexane/ether: mp 36–38° C.; $H^1$-NMR (DMSO-$d_6$)δ 7.88 (s, 1H); 8.35 (s, 1H); 10.11 (s, 1H); MS m/z 231 ($M^+$).

2. 3,4-DFMD-6-aminobenzaldehyde

To a solution of ferrous sulfate (22.5 g, 75.6 mmol) in boiling water (150 mL) was added to a solution of 3,4-DFMD-6-nitrobenzaldehyde (2.1 g, 9 mmol) in EtOAc (25 mL) followed by ammonium hydroxide (27 mL) in portions. The mixture was refluxed for 6 min, cooled, diluted with EtOAc (150 mL), then filtered. The EtOAc layer was washed with brine, dried and concentrated. Purification of the crude product by column chromatography on silica gel provided the title compound (720 mg; 40%): mp 78–79° C.; $^1$H-NMR (DMSO-$d_6$)δ 6.71 (s, 1H), 7.45 (s, 2h), 7.58 (s, 1H), 9.80 (s, 1, CHO).

3. Synthesis of 10,11-Difluoromethylenedioxy-20(S)-camptothecin (10,11-DFMD-20(S)-CPT)

A stirred mixture of the above 3,4-DFMD-6-aminobenzaldehyde (400 mg, 2 mmol), and oxytricyclic ketone (530 mg, 2 mmol) in toluene (75 mL) and glacial acetic acid (0.5 mL) was refluxed for 15 min. p-Toluene sulfonic acid (50 mg) was added and the mixture was heated under reflux for 15 h. Removal of solvents under reduced pressure followed by chromatography of the crude product on silica gel yielded the title compound (590 mg): $^1$H-NMR (DMSO-d6)δ 0.88 (t, 3H, H-18), 1–85 (m, 2H), 5.25 (s, 2H), 5.40 (s, 2H), 6.50 (s, 1H), 7.30 (s, 1H), 8.10 (S, 1H), 8.11 (S, 1H), 8.67 (s, 1H); MS m/z 428 ($M^+$).

4. 7-Ethyl-10,11-DFMD-20(S)-CPT

A stirred suspension of 10,11-DFMD-20(S)-CPT (620 mg), $FeSO_4$ (150 mg), and propionaldehyde (1 mL, excess) in water (10 mL) at −10° C. was treated dropwise over 5 min with concentrated $H_2SO_4$ (5.5 mL). The resulting tan solution was treated at −10° C. with 30% $H_2O_2$ (360 mg) by slow addition. The stirred mixture was left to warm to ambient temperature and after 1 h was poured into cracked ice/$H_2O$. The mixture was extracted several times with $CHCl_3$ and the combined $CHCl_3$ extract was dried, evaporated, and chromatographed using silica gel. The product 7-ethyl-10,11-DFMD-20(S)-CPT was obtained as an off white solid (455 mg, 69%): IR (KBr) 3420, 3095, 1748, 1660 cm$^{-1}$; $^1$H-NMR (DMSO-d6)δ 0.85 (t, 3H), 1.27 (t, 3H), 1.92 (m, 2H), 3.20 (m, 2H), 5.29 (s, 2H), 5.41 (s, 2H), 6.51 (s, 1H), 7.27 (s, 1H), 8.08 (s, 1H ), 8.25 (s, 1H); MS m/z 456 ($M^+$).

5. 10,11-DFMD-20-O-Glycinyl-20(S)-CPT Hydrochloride

A stirred mixture of 10,11-DFMD-CPT (215 mg, 0.5 mmol), BOC-glycine (235 mg, 1.36 mmol), DMAP (40 mg), $CH_2Cl_2$ (150 mL) was treated with DCC (2.2 mL, 1.0M solution of DCC in $CH_2Cl_2$). After 15 h, the reaction mixture was concentrated to 30 mL and filtered. The filtrate containing the CPT-BOC ester was purified by chromotography ($SiO_2$, 25 g, $CHCl_3$). The pure ester was obtained as an off-white solid (257 mg; 87%) $^1$H-NMR (DMSO-$d_6$)δ 0.92 (t, 3H), 1.85 (m, 2H), 1.38 (s, 9H), 4.11 (d, ABq, 2H), 5.22 (s, 2H), 5.38 (s, 2H), 7.28 (s, 1H), 8.08 (s, 1H), 8.11 (s, 1H), 8.65 (s, 1H); MS m/z 585 ($M^+$). The CPT-BOC ester (250 mg, 0.43 mmol) was dissolved in dry $CH_2Cl_2$ (60 mL) and the solution was cooled to 0° C. A solution of HCl (g) saturated dioxane (2.5 mL) was added dropwise. After stirring for 2 h, the product was filtered rapidly, washed with $CH_2Cl_2$, and dried to get a light yellow powder (183 mg, 82%, $^1$H-NMR (DMSO-$d_6$)δ 0.92 (t, 3H), 2.09 (m, 2H), 4.18 (d ABq, 2H), 5.20 (s, 2H), 5.42 (s, 2H), 7.31 (s, 1H), 8.00 (s, 1H), 8.18 (s, 1H), 8.68 (s, 1H), 9.1 (b, 3H).

6. 10-11-DFMD-20-O-N-methylglycinyl-CPT Hydrochloride

A stirred mixture of 10,11-DFMD-CPT (240 mg, 0.56 mmol), BOC-N-methylglycine (240 mg, 1.40 mmol), $CH_2Cl_2$ (150 mL), DMAP (50 mg) was treated with DCC (2.5 mL, 1.0M solution of DCC in $CH_2Cl_2$). After 8 h, the reaction mixture was concentrated to 25 mL and filtered. The filtrate was concentrated and purified by chromatography ($SiO_2$, 25 g, $CHCl_3$). BOC ester was obtained as a beige powder (295 mg, 88%) $^1$H-NMR (DMSO-$d_6$)δ 0.93 (t, 3H), 1.42 (s, 9H), 2.15 (m, 2H), 2.63 (s, 3H), 4.28 (d ABq, 2H), 5.35 (s, 2H), 5.58 (s, 2H), 7.28 (s, 1H), 7.90 (s, 1H), 8.18 (s, 1H), 8.70 (s, 1H); MS m/z 599 ($M^+$). The CPT-BOC ester (280 mg, 0.46 mmol) was dissolved in dry $CH_2Cl_2$ (50 mL) and the solution was cooled to 0° C. HCl (g)/dioxane solution (3 mL) was added in drops. After stirring for 2 h, the suspension was rapidly filtered, washed with $CH_2Cl_2$, and dried to give a yellow powder (212 mg, 85%) $^1$H-NMR (DMSO-$d_6$)δ 0.95 (t, 3H), 2.19 (m, 2H), 2.66 (s, 3H), 4.37 (d ABq, 2H), 5.32 (s,2H), 5.55 (s, 2H), 7.31 (s, 1H), 7.93 (s, 1H), 8.11 (s, 1H), 8.68 (s, 1H).

7. 10,11-DFMD-20-O-NN-dimethylglycinyl-20(S)-CPT Hydrochloride 10,11-DFMD (107 mg, 0.25 mmol) was stirred with N,N-dimethylglycine (51 mg, 0.50 mmol) in $CH_2Cl_2$ (30 mL). An excess of BOP reagent (442 mg) and DMAP (30 mg) were added. This was followed by the addition of triethylamine (200 mg in 2 mL $CH_2Cl_2$). After stirring at room temp for 18 h, the solvent was evaporated and the residue was subjected to column chromatography ($SiO_2$, 15 g, $CHCl_3$) yielding pure DFMD-NN-dimethylglycinyl CPT (93 mg, 72%). $^1$H-NMR (DMSO-$d_6$)δ 0.93 (t, 3H), 2.15 (m, 2H, H-19), 2.60 (s, 6H), 4.35 (d ABq 2H), 5.29 (s, 2H), 5.52 (s, 2H), 7.29 (s, 1H), 7.91 (s, 1H), 8.13 (s, 1H), 8.70 (s, 1H); MS m/z 513 ($M^+$).

This free base was converted to the water soluble hydrochloride salt by dissolving it in $CH_2Cl_2$ (30 mL) and adding HCl (g)/dioxane solution (1 mL). Evaporation of the solvent yielded an orange yellow powder which was washed with $CH_2Cl_2$ and dried (91 mg, 92%) $^1$H-NMR (DMSO-$d_6$)δ 0.95

(t, 3H), 2.2 (m, 2H), 2.69 (s, 6H), 4.42 (d, ABq, 2H), 5.31 (s, 2H), 5.55 (s, 2H), 7.30 (s, 1H), 7.94 (s, 1H), 8.17 (s, 1H), 8.78 (s, 1H).

8. 7-Ethyl-10,11-DFMD-20-O-Glycinyl-20(S)-CPT Hydrochloride

The title compound was prepared as described in Example 5 except that the starting material is 7-ethyl-10,11-DFMD-CPT.

9. 7-Ethyl-10,11-DFMD-20-O-N-methylglycinyl-20(S)-CPT Hydrochloride

The title compound was prepared as described in Example 6 except that the starting material is 7-ethyl-10,11-DFMD-CPT.

10. 7-Ethyl-10,11-DFMD-20-O-N,N-dimethylglycinyl-20(S)-CPT Hydrochloride

The title compound was prepared as described in Example 7 except that the starting material is 7-ethyl-10,11-DFMD-CPT.

11. 7-Hydroxymethyl-10,11-DFMD-20(S)-CPT

To a stirred suspension of 10,11-DFMD-CPT (1.0 g, 2.3 mmol) in MeOH (35 mL) and $H_2O$ (30 mL), 75% $H_2SO_4$ (25 mL) was added dropwise followed by $FeSO_4 7H_2O$ (0.8 g, 2.2 mmol). To the ice cold mixture 30% $H_2O_2$ (5 mL, 2.2 mmol) was added in drops. The mixture was stirred at room temperature for 16 h and poured into ice/$H_2O$. The precipitate was collected, washed with water, and dried. Recrystallization of the solid in $CHCl_3$/MeOH yielded pure 7-hydroxymethyl DFMD as an off-white powder (830 mg, 78%) $^1$H-NMR (DMSO-$d_6$)δ 0.91 (t, 3H), 1.85 (m, 2H), 5.21 (s, 2H), 5.31 (s, 2H), 5.38 (s, 2H), 6.50 (s, 1H ), 7.33 (s, 1H), 8.11 (s, 1H), 8.12 (s, 1H); MS m/z 456 ($M^+$).

12. 7-Bromomethyl-10,11-DFMD-20(S)-CPT

A mixture of 7-hydroxymethyl-10,11-DFMD-CPT (700 mg, 1.5 mmol), HBr (6 mL) and 1 drop of con $H_2SO_4$ was heated at 80–90° C. for 18 h. HBr was removed under reduced pressure and the residue was recrystallized in $CHCl_3$/MeOH to yield the title compound (612 mg, 77%) $^1$H-NMR (DMSO-$d_6$)δ 0.88 (t, 3H), 1.85 (m, 2H), 5.33 (s, 2H), 5.35 (s, 2H), 5.44 (s, 2H), 6.5 (s, 1H), 7.32 (s, 1H), 8.15 (s, 1H), 8.40 (s, 1H); High resolution mass spectrum: calcd. 520:00815. Found: 520:00840.

13. 7-Chloromethyl-10,11-DFMD-20(S)-CPT

A mixture of 7-bromomethyl-DFMD-CPT (0.2 g, 0.38 mmol), an excess of LiCl (250 mg) and acetone (50 mL) was refluxed for 12 h. The solvent was evaporated and the residue was taken in water and filtered. After washing the residue with water, it was dried and recrystallized from $CHCl_3$/MeOH to yield a pale yellow powder (125 mg, 69%) $^1$H-NMR (DMSO-$d_6$)δ 0.90 (t, 3H), 1.90 (m, 2H), 5.33 (s, 2H), 5.44 (s, 4H), 6.50 (s, 1H), 7.32 (s, 1H), 8.32 (s, 1H), 8.45 (s, 1H). High resolution mass spectrum: calcd. 476:05867. Found: 476:05850.

14. 7-Chloromethyl-10,11-DFMD-20(S)-CPT-Glycinyl-20(S)-CPT Hydrochloride

The title compound was prepared as described in Example 5 except that the starting material is 7-chloromethyl-DFMD-20(S)-CPT.

15. 7-Chloromethyl-10,11-DFMD-20-O-N-methylglycinyl-20(S)-CPT Hydrochloride

The title compound was prepared as described in Example 6 except that the starting material is 7-chloromethyl-DFMD-20(S)-CPT.

16. 7-Chloromethyl-10,11-DFMD-20-O-N,N-dimethylglycinyl-20(S)-CPT Hydrochloride

The title compound was prepared as described in Example 7 except that the starting material is 7-chloromethyl-10,11-DFMD-20(S)-CPT.

17. 9-Nitro-10,11-DFMD-20(S)-CPT 10,11-DFMD-20(S)-CPT (400 mg, 0.93 mmol) was stirred in con $H_2SO_4$ (5 mL). The resulting solution was cooled to −5° C. and $KNO_3$ (95 mg) was added. After stirring at that temp for 16 h, it was poured into ice. The solid was collected, washed with ice water, and recrystallized from $CHCl_3$/MeOH as an orange yellow solid (274 mg, 62%) $^1$H-NMR (DMSO-$d_6$)δ 0.91 (t, 3H), 2.23 (m, 2H), 5.31 (s, 2H), 5.43 (s, 2H), 6.52 (s, 1H), 7.29 (s, 1H), 8.22 (s, 1H), 8.49 (s, 1H); MS m/z 473 ($M^+$).

18. 9-Amino-10,11-DFMD-20(S)-CPT

9-Nitro-DFMD-CPT (117 mg, 0.25 mmol) was added to a cold (−10° C.) stirred solution of $SnCl_2$ (170 mg, 0.89 mmol) in conc Hcl (2 mL). After 1.5 h, the mixture was neutralized to pH 6–7 and the solid was collected, washed with $H_2O$, and dried. The powdered solid was dissolved in warm DMF and the resulting solution was concentrated in vacuo to 3–5 mL and the orange solid collected (55 mg, 50%) $^1$H-NMR (DMSO-$d_6$)δ 0.88 (t, 3H), 1.98 (m, 2H), 5.23 (s, 2H), 5.35 (s, 1H), 7.21 (s, 1H), 8.01 (s, 1H), 8.11 (s, H); MS m/z 441 ($M^+$).

19. 7-Ethyl-9-nitro-10,11-DFMD-20(S)-CPT

The title compound was prepared as described in Example 17 except that the starting material was 7-ethyl-10,11-DFMD-20(S)-CPT.

20. 7-Ethyl-9-amino-10,11-DFMD-20(S)-CPT

The title compound was prepared by $SnCl_2$ reduction OF 7-ETHYL-9-NITRO-10,11-DFMD-20(S)-CPT as reported in Example 18.

21. 9-Amino-10,11-DFMD-20-O-Glycinyl-20(S)-CPT Hydrochloride

A stirred solution of 9-nitro-10,11-DFMD-20(S)-CPT (250 mg, 0.57 mmol), BOC-glycine (245 mg, 1.4 mmol), $CH_2Cl_2$ (125 mL), DMAP (35 mg) was treated with DCC (2.5 mL; 1.0 M solution of DCC in $CH_2Cl_2$). After 18 h, the reaction mixture was concentrated to 20 mL and filtered. The filtrate was concentrated and purified by chromatography ($SiO_2$, 25 g, $CHCl_3$). 9-Nitro-10,11-DFMD-CPT-BOC glycine ester was obtained as a light brown powder (270 mg, 81%) $^1$H-NMR (DMSO-$d_6$)δ 0.96 (t, 3H), 1.42 (s, 9H), 2.15 (m, 2H), 4.18 (d ABq, 2H), 5.28 (s, 2H), 5.45 (s, 2H), 7.32 (s,H), 8.14 (s, 1H), 8.32 (s, 1H); MS m/z 630 ($M^+$).

9-Nitro-10,11-DFMD-20(S)-CPT•BOC•Glycine Ester (200 mg, 0.32 mmol) was taken in ethanol (75 mL). 10% Pd/c (75 mg) was added and stirred under $H_2$ for 3 h. After removing Pd/C, the crude product was purified by chromatography ($SiO_2$, 20 g, $CHCl_3$). Pure 9-Nitro-10,11-DFMD-20(S)-CPT•BOC•Glycine Ester was obtained as a light brown powder (150 mg, 79%) MS m/z 600 ($M^+$).

9-Amino-10,11-DFMD-20(S)-CPT•BOC•Glycine Ester (150 mg, 0.25 mmol) was dissolved in dry $CH_2Cl_2$ (70 mL) and the solution was cooled to 0° C. HCl (g)/dioxane solution (2 mL) was added in drops. After stirring for 2 h, the precipitate was rapidly filtered, washed with $CH_2Cl_2$, and dried to give orange brown powder (113 mg, 84%) $^1$H-NMR (DMSO-$d_6$)δ 0.91 (t, 3H), 2.25 (m, 2H), 4.28 (d ABq, 2H), 5.26 (s, 2H), 5.41 (s, 2H), 7.29 (s, 1H), 8.09 (s, 1H), 8.78 (s, 1H).

22. 9-Amino-10,11-DFMD-20-O-N-Methyl-Glycinyl-20(S)-CPT•Hydrochloride

The title compound was prepared as described in Example 21 using BOC-N-methylglycine instead of BOC-glycine.

23. 9-Amino-10,11-DFMD-20-O-N,N-Dimethyl-Glycinyl-20(S)-CPT•Hydrochloride

The title compound was prepared as described in Example 7.

24. 7-Ethyl-9-Amino-10,11-MD-20-O-Glycinyl-20(S)-CPT Hydrochloride

The title compound was prepared as described in Example 21 using 7-ethyl-9-nitro-10,11-DFMD-20(S)-CPT as the starting material.

25. 7-Ethyl-9-Amino-10,11-DFMD-20-O-N-Methylglycinyl-20(S)-CPT Hydrochloride

The title compound was prepared as described in Example 21 using 7-ethyl-9-nitro-10,11-DFMD-20(S)-CPT and BOC-N-methylglycine.

26. 7-Ethyl-9-Amino-10,11-DFMD-20-O-N,N-Dimethylglycinyl-20(S)-CPT Hydrochloride The title compound was prepared as described in Example 7.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A camptothecin compounds having the structure:

where

X and Y are each independently $NO_2$, $NH_2$, H, F, Cl, Br, I, COOH, OH, O—$C_{1-6}$alkyl, SH, S—$C_{1-6}$alkyl, CN, NH—$C_{1-6}$alkyl, N($C_{1-6}$alkyl)$_2$, CHO, $C_{1-8}$alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$alkyl$)_2$ wherein Z is selected from the group consisting of O, NH and S, and a is an integer of 2 or 3, —$CH_2$—L, where L is halogen (F, Cl, Br, I), $^+N_2$, $^+(OR^1)_2$, $^+S(R^1)_2$, $^+N(R^1)_3$, $OC(O)R^1$, $OSO_2R^1$, $OSO_2CF_3$, $OSO_2C_4F_9$, $C_{1-6}$alkyl-C(=O)—, $C_{4-18}$aryl—C(=O)—, $C_{1-6}$alkyl-$SO_2$—, perfluoro $C_{1-6}$alkyl-$SO_2$— and $C_{4-18}$aryl-$SO_2$—, (where each $R^1$ independently is $C_{1-6}$alkyl, $C_{4-18}$aryl or $C_{4-18}$Ar$C_{1-6}$alkyl); or —$CH_2NR^2R^3$, where (a) $R^2$ and $R^3$ are, independently, hydrogen, $C_{1-6}$alkyl, $C_{3-7}$ cycloalkyl, $C_{3-7}$cycloalkyl-$C_{1-6}$alkyl, $C_{2-6}$alkenyl, hydroxy-$C_{1-6}$alkyl, $C_{1-6}$alkoxy-$C_{1-6}COR^4$ where $R^4$ is hydrogen, $C_{1-6}$alkyl, perhalo-$C_{1-6}$alkyl, $C_{3-7}$cycloalkyl, $C_{3-7}$cycloalkyl-$C_{1-6}$alkyl, $C_{2-6}$alkenyl, hydroxy-$C_{1-6}$alkyl, $C_{1-6}$alkoxy, $C_{1-6}$alkoxy-$C_{1-6}$alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$alkyl, perhalo-$C_{1-6}$alkyl, aryl, aryl substituted with one or more groups selected from the group consisting of $C_{1-6}$alkyl, halogen, nitro, amino, $C_{1-6}$alkylamino, perhalo-$C_{1-6}$alkyl, hydroxy-$C_{1-6}$alkyl, $C_{1-6}$alkoxy, $C_{1-6}$alkoxy-$C_{1-6}$alkyl and —$COR^6$ where $R^6$ is hydrogen, $C_{1-6}$alkyl perhalo-$C_{1-6}$alkyl, $C_{1-6}$alkoxy, aryl, and aryl substituted with one or more $C_{1-6}$alkyl, perhalo-$C_{1-6}$alkyl, hydroxy-$C_{1-6}$alkyl, or $C_{1-6}$alkoxy-$C_{1-6}$alkyl groups;

$R^7$ is H, or C(O)—$(CH_2)_m$—$NR^8R^9$, where m is an integer of 1–6 or —C(O)$CHR^{10}NR^8R^9$, where $R^{10}$ is the side chain of one of the naturally occurring α amino acids, $R^8$ and $R^9$ are, independently, hydrogen, $C_{1-8}$alkyl or —C(O)$CHR^{11}NR^{12}R^{13}$, where $R^{11}$ is the side chain of one of the naturally occurring α-amino acids and $R^{12}$ and $R^{13}$ are each independently hydrogen or $C_{1-8}$alkyl; and n is an integer of 1 or 2.

2. The camptothecin compound of claim 1, wherein n is 1.

3. The camptothecin compound of claim 1, wherein L is selected from the group consisting of Cl, Br and I.

4. The camptothecin compound of claim 1, wherein $R^7$ is C(O)—$(CH_2)_m$—$NR^8R^9$, where m is an integer of 1–6 or —C(O)$CHR^{10}NR^8R^9$, where $R^{10}$ is the side chain of one of the naturally occurring α-amino acids, $R^8$ and $R^9$ are, independently, hydrogen, $C_{1-8}$alkyl or —C(O)$CHR^{11}NR^{12}R^{13}$, where $R^{11}$ is the side chain of one of the naturally occurring α-amino acids and $R^{12}$ and $R^{13}$ are each independently hydrogen or $C_{1-8}$alkyl.

5. The camptothecin compound of claim 1, which is selected from the group consisting of 10,11-difluoromethylenedioxy-20(S)-camptothecin; 7-ethyl 10,11-difluoromethylenedioxy-20-(S)-camptothecin; 7-chloromethyl 10,11-difluoromethylenedioxy-20-(S)-camptothecin; 7-bromomethyl 10,11-difluoromethylenedioxy-20-(S)-camptothecin; 7-hydroxymethyl-10,11-difluoromethylenedioxy-20-(S)-camptothecin, 9-nitro 10,11-difluoromethylenedioxy-20-(S)-camptothecin, 9-amino 10,11-difluoromethylenedioxy-20-(S)-camptothecin, 7-ethyl-9-nitro 10,11-difluoromethylenedioxy-20-S)-camptothecin, 7-ethyl-9-amino 10,11-difluoromethylenedioxy-20-(S)-camptothecin, 10,11-difluoromethylenedioxy-20-O-glycinyl-20-(S)-camptothecin; 7-ethyl 10,11-difluoromethylenedioxy-20-O-glycinyl-20-(S)-camptothecin; 7-chloromethyl 10,11-difluoromethylenedioxy-20-O-glycinyl-20-(S)-camptothecin; 7-bromomethyl 10,11-difluoromethylenedioxy-20-O-glycinyl-20-(S)-camptothecin; 7-hydroxymethyl-10,11-difluoromethylenedioxy-20-O-glycinyl-20-(S)-camptothecin; 9-nitro 10,11-difluoromethylenedioxy-20-O-glycinyl-20-(S)-camptothecin; 9-amino 10,11-difluoromethylenedioxy-20-O-glycinyl-20-(S)-camptothecin; 7-ethyl-9-nitro 10,11-difluoromethylenedioxy-20-O-glycinyl-20-(S)-camptothecin; 7-ethyl-9-amino 10,11-difluoromethylenedioxy-20-O-glycinyl-20-(S)-camptothecin;

10,11-difluoromethylenedioxy-20-O-N-methylglycinyl-20-(S)-camptothecin; 7-ethyl 10,11-difluoromethylenedioxy-20-O-N-methylglycinyl-20-(S)-camptothecin; 7-chloromethyl 10,11-difluoromethylenedioxy-20-O-N-methylglycinyl-20-(S)-camptothecin; 7-bromomethyl 10,11-difluoromethylenedioxy-20-O-N-methylglycinyl-20-(S)-camptothecin; 7-hydroxymethyl-10,11-difluoromethylenedioxy-20-O-N-methylglycinyl-20-(S)-camptothecin; 9-nitro 10,11-difluoromethylenedioxy-20-O-N-methylglycinyl-20-(S)-camptothecin; 9-amino 10,11-difluoromethylenedioxy-20-O-N-methylglycinyl-20-(S)-camptothecin; 7-ethyl-9-nitro 10,11-difluoromethylenedioxy-20-O-N-methylglycinyl-20-(S)-camptothecin; 7-ethyl-9-amino 10,11-difluoromethylenedioxy-20-O-N-methylglycinyl-20-(S)-camptothecin;

10,11-difluoromethylenedioxy-20-O-N,N-dimethylglycinyl-20-(S)-camptothecin; 7-ethyl 10,11-difluoromethylenedioxy-20-O-N,N-dimethylglycinyl-20-(S)-camptothecin; 7-chloromethyl 10,11-difluoromethylenedioxy-20-O-N,N-dimethylglycinyl-20-(S)-camptothecin; 7-bromomethyl 10,11-difluoromethylenedioxy-20-O-N,N-dimethylglycinyl-20-(S)-camptothecin; 7-hydroxymethyl-10,11-difluoromethylenedioxy-20-O-N,N-dimethylglycinyl-20-(S)-camptothecin; 9-nitro 10,11-difluoromethylenedioxy-20-O-N,N-dimethylglycinyl-20-(S)-camptothecin; 9-amino 10,11-difluoromethylenedioxy-20-O-N,N-dimethylglycinyl-20-(S)-camptothecin; 7-ethyl-9-nitro 10,11-difluoromethylenedioxy-20-O-N,N-dimethylglycinyl-20-(S)-camptothecin; 7-ethyl-9-amino 10,11-difluoromethylenedioxy-20-O-N,N-dimethylglycinyl-20-(S)-camptothecin;

10,11-difluoromethylenedioxy-20-O-β-ala-lys-20-(S)-camptothecin; 7-ethyl 10,11-difluoromethylenedioxy-20-O-β-ala-lys-20-(S)-camptothecin; 7-chloromethyl 10,11-difluoromethylenedioxy-20-O-β-ala-lys-20(S)-camptothecin; 7-bromomethyl 10,11-difluoromethylenedioxy-20-O-β-ala-lys-20-(S)-camptothecin; 7-hydroxymethyl-10,11-difluoromethylenedioxy-20-O-β-ala-lys-20-(S)-camptothecin, 9-nitro 10,11-difluoromethylenedioxy-20-O-β-ala-lys-20-(S)-camptothecin, 9-amino 10,11-difluoromethylenedioxy-20-O-β-ala-lys-20-(S)-camptothecin, 7-ethyl-9-nitro 10,11-difluoromethylenedioxy-20-O-β-ala-lys-20-(S)-camptothecin and 7-ethyl-9-amino 10,11-difluoromethylenedioxy-20-O-β-ala-lys-20-(S)-camptothecin;

10,11-difluoromethylenedioxy-20-O-β-ala-20-(S)-camptothecin; 7-ethyl 10,11-difluoromethylenedioxy-20-O-β-ala-20-(S)-camptothecin; 7-chloromethyl 10,11-difluoromethylenedioxy-20-O-β-ala-20-(S)-camptothecin; 7-bromomethyl 10,11-difluoromethylenedioxy-20-O-β-ala-20-(S)-camptothecin; 7-hydroxymethyl-10,11-difluoromethylenedioxy-20-O-β-ala-20-(S)-camptothecin; 7-hydroxymethyl-10,11-difluoromethylenedioxy-20-O-β-ala-20-(S)-camptothecin, 9-amino 10,11-difluoromethylenedioxy-20-O-β-ala-20-(S)-camptothecin, 7-ethyl-9-nitro 10,11-difluoromethylenedioxy-20-O-β-ala-20-(S)-camptothecin and 7-ethyl-9-amino 10,11-difluoromethylenedioxy-20-O-β-ala-20-(S)-camptothecin.

6. A method of treating leukemia or solid tumors comprising administering to a patient in need thereof, a therapeutically effective amount of the camptothecin compound of claim 1.

7. A pharmaceutical composition comprising the camptothecin compound of claim 1.

8. A method for inhibiting the enzyme topoisomerase I, comprising contacting a DNA-topoisomerase I complex with the camptothecin compound of claim 1.

9. A method of preparing a camptothecin compound comprising:

condensing a compound of formula II

(II)

with a tricyclic ketone of formula III

(III)

to form a camptothecin compound of structure n is an integer of 1 or 2.

10. A camptothecin compounds having the structure:

where

X and Y are each independently $NO_2$, $NH_2$, H, F, Cl, Br, I, COOH, OH, O—$C_{1-6}$alkyl, SH, S—$C_{1-6}$alkyl, CN, NH—$C_{1-6}$alkyl, N($C_{1-6}$alkyl)$_2$, CHO, $C_{1-8}$alkyl, $N_3$, —Z—$(CH_2)_a$—N—$((CH_2)_b OH)_2$, wherein Z is selected from the group consisting of O, NH and S, and a and b are each independently an integer of 2 or 3, —Z—$(CH_2)_a$—N—$(C_{1-6}alkyl)_2$ wherein Z is selected from the group consisting of O, NH and S, and a is an integer of 2 or 3, —$CH_2$—L, where L is halogen (F, Cl, Br, I), $^+N_2$, $^+(OR^1)_2$, $^+S(R^1)_2$, $^+N(R^1)_3$, $OC(O)R^1$, $OSO_2R^1$, $OSO_2CF_3$, $OSO_2C_4F_9$, $C_{1-6}$alkyl—C(=O)—, $C_{4-18}$aryl—C(=O)—, $C_{1-6}$alkyl-$SO_2$—, perfluoro $C_{1-6}$alkyl-$SO_2$— and $C_{4-18}$aryl-$SO_2$—, (where each $R^1$ independently is $C_{1-6}$alkyl, $C_{1-18}$ aryl or $C_{4-18}$ Ar$C_{1-6}$alkyl); or —$CH_2NR^2R^3$, where (a) $R^2$ and $R^3$ are, independently, hydrogen, $C_{1-6}$alkyl, $C_{3-7}$cycloalkyl, $C_{3-7}$cycloalkyl-$C_{1-6}$alkyl, $C_{2-6}$alkenyl, hydroxy- $C_{1-6}$alkyl, $C_{1-6}$alkoxy-$C_{1-6}COR^4$ where $R^4$ is hydrogen, $C_{1-6}$alkyl, perhalo-$C_{1-6}$alkyl, $C_{3-7}$cycloalkyl, $C_{3-7}$cycloalkyl-$C_{1-6}$alkyl, $C_{2-6}$alkenyl, hydroxy-$C_{1-6}$alkyl, $C_{1-6}$alkoxy, $C_{1-6}$alkoxy-$C_{1-6}$alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$alkyl, perhalo-$C_{1-6}$alkyl, aryl, aryl substituted with one or more groups selected from the group consisting of $C_{1-6}$alkyl, halogen, nitro, amino, $C_{1-6}$alkylamino, perhalo-$C_{1-6}$alkyl, hydroxy-$C_{1-6}$alkyl, $C_{1-6}$alkoxy, $C_{1-6}$alkoxy-$C_{1-6}$alkyl and —$COR^6$ where $R^6$ is hydrogen, $C_{1-6}$alkyl perhalo-$C_{1-6}$alkyl, $C_{1-6}$alkoxy, aryl, and aryl substituted with one or more $C_{1-6}$alkyl, perhalo-$C_{1-6}$alkyl, hydroxy-$C_{1-6}$alkyl, or $C_{1-6}$alkoxy-$C_{1-6}$alkyl groups;

$R^7$ is H, or $C(O)$—$(CH_2)_m$—$NR^8R^9$, where m is an integer of 1–6 or —$C(O)CHR^{10}NR^8R^9$, where $R^{10}$ is the side chain of one of the naturally occurring α-amino acids, $R^8$ and $R^9$ are, independently, hydrogen, $C_{1-8}$alkyl or —$C(O)CHR^{11}NR^{12}R^{13}$, where $R^{11}$ is the side chain of one of the naturally occurring α-amino acids and $R^{12}$ and $R^{13}$ are each independently hydrogen or $C_{1-8}$alkyl; and n is an integer of 1 or 2, wherein Y is —$CH_2$—L.

* * * * *

UNITED STATES PATENT AND TRADEMARK OFFICE
CERTIFICATE OF CORRECTION

PATENT NO.    : 6,268,375 B1
DATED         : July 31, 2001
INVENTOR(S)   : Wall et al.

It is certified that error appears in the above-identified patent and that said Letters Patent is hereby corrected as shown below:

Column 2,
Line 49, "$^+(OR^1)_2, {}^+(NR^1)_3,$", should read -- $^+(OR^1)_2, {}^+S(R^1)_2, {}^+(NR^1)_3,$ --.

Column 3,
Line 44, "m ore", should read -- more --.

Column 4,
Line 57, "$S(R^1)_2,$", should read -- $^+S(R^1)_2,$ --.

Column 5,
Line 22, "asparate", should read -- aspartate --.
Line 40, "1988", should read -- 1998 --.
Line 49, "to intorduced" should read -- to be introduced --.

Column 6,
Line 11, "O-(S)", should read -- O-glycinyl-(S) --.
Line 16, "20-glycinyl", should read -- 20-O-glycinyl --.
Line 21, "S)", should read -- (S) --.

Column 7,
Line 13, "S)", should read -- (S) --.

Column 8,
Line 21, "such a", should read -- such as --.

Column 9,
Line 21, "tryptophan, leucine, arginine", should read -- tryptophan, arginine --.
Line 22, "asparatate", should read -- aspartate --.

Column 10,
Line 4, "an", should read -- and --.

Column 12,
Line 4, "elixers", should read -- elixirs --.
Line 66, "color", should read -- colon --.

Column 13,
Line 2, "active", should read -- activity --.
Line 8, "maleria", should read -- malaria --.

UNITED STATES PATENT AND TRADEMARK OFFICE
CERTIFICATE OF CORRECTION

PATENT NO.   : 6,268,375 B1
DATED        : July 31, 2001
INVENTOR(S)  : Wall et al.

It is certified that error appears in the above-identified patent and that said Letters Patent is hereby corrected as shown below:

Column 16,
Line 27, "OF", should read -- of --.

Column 17,
Line 43, "$^{+N}_2$", should read -- $^+N_2$ --.

Column 18,
Line 3, "αamino" should read -- α-amino --.

Column 19,
Line 47, "camptothecin, 9-amino", should read -- camptothecin, 9-nitro 10,11-difluoromethylenedioxy– 20-O-β-ala-20-(S)-camptothecin, 9-amino --.
Lines 47-50, "camptothecin, 7-hydroxymethyl-10,11-difluoromethylenedioxy-20– O-β-ala-20-(S)-camptothecin, 9-amino", should read -- camptothecin, 9-amino --.

Column 20,
Line 36, "compounds", should read -- compound --.
Line 63, "$C_{1-18}$", should read -- $C_{4-18}$ --.

Signed and Sealed this

Twenty-seventh Day of August, 2002

*Attest:*

*Attesting Officer*

JAMES E. ROGAN
*Director of the United States Patent and Trademark Office*